(12) United States Patent
Rahman et al.

(10) Patent No.: US 11,237,127 B1
(45) Date of Patent: Feb. 1, 2022

(54) NANOCOMPOSITE AS AN ELECTROCHEMICAL SENSOR

(71) Applicant: King Abdulaziz University, Jeddah (SA)

(72) Inventors: Mohammed Muzibur Rahman, Jeddah (SA); Abdullah Mohamed Asiri, Jeddah (SA); Muhammad Tariq Saeed Chani, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/360,020

(22) Filed: Jun. 28, 2021

(51) Int. Cl.
*G01N 27/30* (2006.01)
*G01N 27/49* (2006.01)
*G01N 33/00* (2006.01)
*G01N 33/18* (2006.01)

(52) U.S. Cl.
CPC .......... *G01N 27/308* (2013.01); *G01N 27/49* (2013.01); *G01N 33/0047* (2013.01); *G01N 33/1826* (2013.01)

(58) Field of Classification Search
CPC .. G01N 27/308; G01N 27/3278; G01N 27/48; G01N 27/49; G01N 33/0047; G01N 33/1826
See application file for complete search history.

(56) References Cited

U.S. PATENT DOCUMENTS

2021/0023221 A1   1/2021   Cui et al.

OTHER PUBLICATIONS

Beduk et al., "A paper-based inkjet-printed PEDOT:PSS/ZnO sol-gel hydrazine sensor," Sensors and Actuators B: Chemical 306 (2020) 127539 (Year: 2020).*
Hardi et al., "Amperometric Detection of Dopamine based on a Graphene Oxide/PEDOT:PSS Composite Electrode," International Journal of Technology 11)5) 974-983 (2020) (Year: 2020).*
Rattanaveeranon et al., "Effect of Durian Peel Ash Added in Zinc Oxide/Reduced Graphene Oxide Composites Used as a Chemical Sensor for Hydrazine Detection," Materials Sciences and Applications, Feb. 23, 2021, 12, 111-120 (Year: 2021).*
Tukimin et al., "Electrodeposition of poly(34-ethylenedioxythiophene)/reduced graphene oxide/manganese dioxide for simultaneous detection of uric oxide, dopamine and ascorbic acid," Journal of Electroanalytical Chemistry 820 (2018) 74-81 (Year: 2018).*
Yasri et al,"Highly selective mercury detection at partially oxidized graphene/poly(3,4-ethylenedioxythiophene):poly(styrenesulfonate) nanocomposite film-modified electrode," frontiers in Materials Dec. 2014|vol. 1 |Article 33 (Year: 2014).*
Faisal et al., "Polythiophene/ZnO nanocomposite-modified glassy carbon electrode as efficient electrochemical hydrazine sensor," Materials Chemistry and Physics 214 (2018) 126-134 (Year: 2018).*

(Continued)

*Primary Examiner* — Alexander S Noguerola
(74) *Attorney, Agent, or Firm* — W&C IP (57) ABSTRACT

An electrochemical sensor is provided wherein the sensor includes a nanocomposite comprising zinc oxide nanoparticles, graphene oxide, and PEDOT:PSS binder polymer, wherein the nanocomposite is deposited as a film on a glassy carbon electrode. The sensor may be included in an electrochemical cell useful for methods of detecting phenylhydrazine in a solution.

9 Claims, 8 Drawing Sheets

(56) References Cited

OTHER PUBLICATIONS

Alam et al., "Fabrication of phenylhydrazine sensor with V2O5 doped ZnO nanocomposites", Materials Chemistry and Physics 243 (Jan. 10, 2020) 122658.
Ding et al., "Hydrothermal synthesis of zinc oxide-reduced graphene oxide nanocomposites for an electrochemical hydrazine sensor", RSC Advances, 2015, 5, 22935.
Jain et al., "Zinc oxide nanoparticle incorporated on graphene oxide: an efficient and stable photocatalyst for water treatment through the Fenton process", Advanced Composites and Hybrid Materials 3 (May 16, 2020), 231-242.
Manivannan et al., "An effective electrochemical detection of chlorogenic acid in real samples: Flower-like ZnO surface covered on PEDOT:PSS composites modified glassy carbon electrode", Sensors and Actuators B: Chemical 301, Dec. 12, 2019, 127002.
Sebastian et al., "Electrochemical detection of an antibiotic drug chloramphenicol based on a graphene oxide/hierarchical zinc oxide nanocomposite", Inorganic Chemistry Frontiers, 2019, 6, 82-93.
Sharma et al., "Fe/La/Zn nanocomposite with graphene oxide for photodegradation of phenylhydrazine", Journal of Molecular Liquids 285 (2019) 362-374.

\* cited by examiner

NANOCOMPOSITE AS AN ELECTROCHEMICAL SENSOR

FIELD OF THE INVENTION

The invention is generally related a nanocomposite comprising graphene oxide (GO), ZnO particles, and PEDOT:PSS polymers for the electrochemical sensing of phenylhydrazine.

BACKGROUND OF THE INVENTION

Generally, phenylhydrazine is an industrially important chemical useful for the preparation of various complex products such as pesticides, pharmaceutical intermediates, chemical blowing agents, photography chemicals, aerospace fuel, and dyes [1]. Phenylhydrazine is also used for the synthesis of plastics foaming agents, antioxidant agents, polymer ingredients and for fabrication of rocket propellant and corrosion inhibitors in the boiler water system [2]. But, phenylhydrazine is considered an environmental toxin and is responsible for some harmful effects in human as well as in plants and environmental species [3-5]. Phenylhydrazine can have harmful effects on the liver and kidney and it can also cause irritation to the eyes, throat, skin, nose, in addition to causing dizziness and temporary blindness [7-11]. The WHO (World Health Organization) and EPA (Environmental Protection Agency), have classified phenylhydrazine as a B2 agent (human carcinogen) [12]. Therefore, it is necessary to find a reliable, efficient, sensitive and user-friendly methods to detect phenylhydrazine, even at the ppm level. The traditional instrumental methods for toxin detection which include spectrophotometry [13, 14], capillary electrophoresis [15], chromatography [16], and chemiluminescence [17] are time-consuming and expensive.

Due to advantages such as low fabrication cost, chemical and photochemical stabilities and good electrochemical activities, nanostructured semiconductor metal oxides were widely implemented in the field of chemical sensors [19]. Various sensor materials such as $SnO_2$ [20, 21], ZnO [22, 23], $In_2O_3$ [24, 25], $Fe_2O_3$ [26], $Co_3O_4$ [27], $TiO_2$ [28], and $WO_3$ [29] were investigated as smart electron mediating agents for chemical sensing. Among these, ZnO with a 3.3 eV band-gap is broadly applied as a phenylhydrazine sensing material. Advantages include cheap devising cost, higher electron mobility, and moderate thermo-chemical stability [30, 31]. Another report claimed that $TiO_2$ showed good sensitivity with a lower limit of detection [32].

However, improved materials for the enhanced detection of phenylhydrazine are still needed.

SUMMARY

Described herein is a nanocomposite comprising graphene oxide (GO) and ZnO for the detection and quantification of phenylhydrazine. The composite utilizes electron mediation by GO during the sensing action of the semiconductor ZnO counterpart.

An aspect of the disclosure provides an electrochemical sensor, comprising a nanocomposite comprising zinc oxide nanoparticles, graphene oxide, and poly(3,4-ethylenedioxythiophene) polystyrene sulfonate (PEDOT:PSS) binder polymer, wherein the nanocomposite is deposited as a film on a glassy carbon electrode. In some embodiments, a diameter of the nanocomposite is 5-10 nm. In some embodiments, the film has a thickness of 0.1-1.0 μm. In some embodiments, the nanocomposite has a band-gap energy of 2-6 eV. In some embodiments, the nanocomposite has a linear dynamic range of 0.1 nM to 1.0 mM.

Another aspect of the disclosure provides an electrochemical cell, comprising an electrochemical sensor as described herein and a counter electrode. In some embodiments, the counter electrode is platinum.

Another aspect of the disclosure provides a method for detecting phenylhydrazine in a solution, comprising contacting the solution with an electrochemical cell as described herein and detecting a change in current indicative of phenylhydrazine transformation. In some embodiments, the solution is at a pH of 7.3-7.7. In some embodiments, the change in current is detected within 10 seconds of the contacting step. In some embodiments, the concentration of phenylhydrazine in the solution is less than 0.03 nM.

DETAILED DESCRIPTION

Embodiments of the disclosure provide zinc oxide and graphene oxide composites prepared by a facile wet-chemical method in alkaline medium at ambient conditions. The ZnO semiconductor nanoparticles are encapsulated within the GO matrices. A simple wet-coating technique may be used to deposit a film comprising ZnO/GO bound with the conducting poly(3,4-ethylenedioxythiophene) polystyrene sulfonate (PEDOT:PSS) polymer onto a glassy carbon electrode (GCE). The electrode has excellent physicochemical stability and may be used as a phenylhydrazine (PHyd) electrochemical sensor at room conditions. As shown in the Example, the working electrode comprising PEDOT:PSS/ZnO/GO NCs deposited on a GCE demonstrated a high sensitivity of 43.8169 μA $mM^{-1}cm^{-2}$ and a very low concentration of detection (0.022 nM). Thus, the chemical sensor described herein may be used to detect environmentally unsafe and hazardous chemicals concomitantly threating the ecology and human health.

The term "nanoparticles" refers to particles which have sizes on the order of nanometer, and which can be dispersed in, and isolated from and re-dispersed in, various solvents in a nanoparticle state, i.e., which are discrete particles (particles that cannot be isolated from a dispersoid or dispersion and particles that cannot be isolated from and re-dispersed in the dispersoid or dispersion are not included in the category of the "nanoparticles"). The nanoparticles have an average particle size (i.e. diameter) of preferably 500 nm or less, more preferably 200 nm or less, more preferably 100 nm or less, or specifically more preferably 50 nm or less. There is no particular limitation on the lower limit, but it is practical to employ an average particle size of 10 nm or more.

Graphene oxide (GO) is a compound of carbon, oxygen, and hydrogen in variable ratios, obtained by treating graphite with strong oxidizers. The maximally oxidized bulk product is a yellow solid with C:O ratio between 2.1 and 2.9, that retains the layer structure of graphite but with a much larger and irregular spacing. The bulk material spontaneously disperses in basic solutions or can be dispersed by sonication in polar solvents to yield monomolecular sheets, the single-layer form of graphite. GO has a large surface area of about 2600 $m^2$/g, extraordinary electrical, thermal and mechanical properties including 3000 W m/K thermal conductivity, and a hydrophilic nature. As used herein "graphene oxide" does not include reduced graphene oxide.

A description of GO sheet structure is given by a model updated by Gao et al. (*Nat Chem*, 2009). This model represents each GO particle by the basal plane of $sp^3$ hybridized carbon atoms with chemically bonded hydroxyl and epoxy functional groups situated in close proximity to each other on both sides of the plane. Edges of basal plane are terminated by carboxyl groups five or six membered lactol (O—C—O) rings, ketone and ester of tertiary alcohol. The mean content of edge functionalities inversely depends on the size of GO particles.

PEDOT:PSS is a polymer mixture of two ionomers. One component in this mixture is made up of sodium polystyrene sulfonate which is a sulfonated polystyrene. Part of the sulfonyl groups are deprotonated and carry a negative charge. The other component poly(3,4-ethylenedioxythiophene) (PEDOT) is a conjugated polymer and carries positive charges and is based on polythiophene. Together the charged macromolecules form a macromolecular salt. PEDOT:PSS can be prepared by mixing an aqueous solution of PSS with EDOT monomer, and to the resulting mixture, a solution of sodium persulfate and ferric sulfate.

In some embodiments, a diameter of the PEDOT:PSS/ZnO/GO aggregated nanocomposite is 5-10 nm, e.g. 7-9 nm, e.g. about 7.9 nm. The the PEDOT:PSS/ZnO/GO nanocomposite is deposited as a film on a glassy carbon electrode to produce an electrochemical sensor. In some embodiments, the film has a thickness of 0.1-1.0 µm, e.g. 0.3-0.7 µm, e.g. about 0.5 µm. In some embodiments, the nanocomposite has a band-gap energy of 2-6 eV, e.g. 3-5 eV, e.g. about 4.23 eV. In some embodiments, the nanocomposite has a linear dynamic range of 0.1 nM to 1.0 mM.

In some embodiments, the ratio of PEDOT:PSS to ZnO/GO is from 2:1 to 1:2, e.g. about 1:1.

Glass-like carbon, often called glassy carbon or vitreous carbon, is a non-graphitizing, or nongraphitizable, carbon which combines glassy and ceramic properties with those of graphite. Properties include high temperature resistance, hardness (7 Mohs), low density, low electrical resistance, low friction, low thermal resistance, extreme resistance to chemical attack, and impermeability to gases and liquids. Glassy carbon can be fabricated in different shapes, sizes and sections. Vitreous carbon can also be produced as a foam, called reticulated vitreous carbon (RVC) which is used as a thermally insulating, microporous glassy carbon three dimensional electrode material.

Embodiments include methods of preparing a composite as described herein. The composite may be synthesized via a wet-chemical method in alkaline medium at ambient conditions.

Embodiments also provide an electrochemical cell comprising an electrochemical sensor as described herein and a counter electrode to form a two-electrode system. Suitable counter electrodes, also known as auxiliary electrodes, include, but are not limited to, platinum, gold, and carbon.

Embodiments also provide methods for detecting phenylhydrazine in a solution, comprising contacting the solution with an electrochemical cell as described herein and detecting a change in current indicative of phenylhydrazine transformation. In some embodiments, the solution is at a pH of 7.3-7.7, e.g. about 7.5. In some embodiments, the change in current is detected within 10 seconds of the contacting step, e.g. 5-10 seconds, e.g. at least about 8-10 seconds. In some embodiments, the concentration of phenylhydrazine in the solution is less than 0.03 nM.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

In this example, poly(3,4-ethylenedioxythiophene) polystyrene sulfonate (PEDOT:PSS) polymers coated low-dimensional zinc oxide nanoparticles decorated graphene oxide nanocomposites (PEDOT:PSS/ZnO/GO NCs) were synthesized by an easy and facile solution method in basic system. The prepared nanocomposite sample was formed by gradual nucleation and growth in mild conditions. Various analyzing tools such as TEM, UV/vis., FTIR, EDS, CV, EIS, XPS, and powder XRD study have been used to characterize the prepared ZnO/GO NCs in detail. The working electrode functioning as a probe of selective phenylhydrazine (PHyd) chemical sensor was prepared on a flat GCE (glassy carbon electrode) as a thin film of ZnO/GO NCs chemically modified by PEDOT:PSS conductive polymers. The fabricated PEDOT:PSS/ZnO/GO NCs/GCE sensor probe exhibited excellent functionalities including higher sensitivity, detection range in lower concentration, high physicochemical stability, reproducibility, large and linear dynamic range of detection and quick response time. The PHyd sensor was implemented with PEDOT:PSS/ZnO/GO NCs/GCE sensor probe to selectively detect PHyd in various environmental and extracted samples.

Materials and Methods

All the chemicals including PHyd, M-tolayl hydrazine (M-THyd), methanol, bisphenol (BPA), 4-methoxy phenol (4-MP), 3-methyl aniline (3-MA), 3-methoxyphenylhydrazine (3-MPHyd), 2,4-dinitrophenol (2.4-DNP), 3-chlorophenol (3-CP), ammonium hydroxide (AH), poly(3,4-ethylenedioxythiophene) polystyrene sulfonate (PEDOT:PSS), mono- as well as di-sodium phosphate were brought from Sigma-Aldrich company. They were used without further purification. To examine the UV-vis and FTIR spectrums, the prepared ZnO/GO NCs were analyzed on thermo scientific FTIR spectrometer (NICOLET iS50, Madison, Wis., USA) and a 300 UV/Visible spectrophotometer (Thermo scientific), respectively. The interatomic binding energies being another important criterion for investigation of chemical and electronic states, were taken under investigation. Therefore, the newly prepared ZnO/GO NCs were analyzed by XPS study using a K-α1 spectrometer (Thermo scientific, K-α1 1066) fitted with radiation source for excitation (Al Kα1, Beam spot size=300.0 μm, pass energy=200.0 eV, pressure~$10^{-8}$ Torr) to measure the binding energies among Zn, C and O. The bonding properties including the molecular properties, nature of the components, and morphology of the solid phase are the major identical tool for ZnO/GO NCs characterization. Therefore, the synthesized NCs were investigated by using a FESEM (JEOL, Japan, JSM-7600F) coupled with XEDS facilities. The structural crystallinity and phase (of the nanoparticles) identification being another categorization of nanoparticles, were taken under consideration by applying XRD examination of the synthesized NCs at ambient condition. The electrochemical method is applied to detect PHyd quantitatively at the desired range of potential scanned by a Keithley electrometer (6517A, USA). The calcined ZnO/GO NCs (coating with PEDOT:PSS) assembly on GCE has functioned as the main working electrode with the desired responsive phosphate buffer system.

Synthesis of the ZnO/GO Nanocomposites

The NCs of ZnO/GO were synthesized from the starting precursors zinc chloride (ZnCl$_2$), graphene oxide (GO), and NH$_4$OH by an easily affordable hydrothermal method. For the formation of hybrid nanostructured materials, the low-temperature wet-chemical method is an established technique and the nanomaterials formed by this method usually have a smaller particle size with reasonable smaller phase formation. In a typical method, a 250.0 ml conical flask was occupied by 100.0 ml deionized water (DI) and a measured quantity of GO and ZnCl$_2$. The mixture was dissolved with vigorous magnetic stirring (MS) for 30 mins. To regulate the pH at 10.5, NH$_4$OH was added dropwise to the solution and the whole conical flask was placed at 150° C. in an oven with continued stirring. At the end, the prepared ZnO/GO NCs was put in a muffle furnace at 500° C. around 6 hours for calcination. For detailed characterization of the synthesized ZnO/GO sample, FTIR, XRD, XPS, and FESEM analysis were accomplished.

$$NH_4OH_{(s)} \rightarrow NH_4^+{}_{(aq)} + OH^-{}_{(aq)} \qquad (i)$$

$$ZnCl_{2(s)} \rightarrow Zn^{2+}{}_{(aq)} + 2Cl^-{}_{(aq)} \qquad (ii)$$

$$NH_4^+{}_{(aq)} + 2OH^-{}_{(aq)} + Zn^{2+}{}_{(aq)} + Cl^-{}_{(aq)} \rightarrow Zn(OH)_{2(aq)} \downarrow + NH_4Cl_{(aq)} \qquad (iii)$$

$$GO\ (dispersed) + Zn(OH)_{2(aq)} \downarrow \rightarrow ZnO/GO_{(s)} \downarrow + H_2O_{(aq)} \qquad (iv)$$

Figure 7:
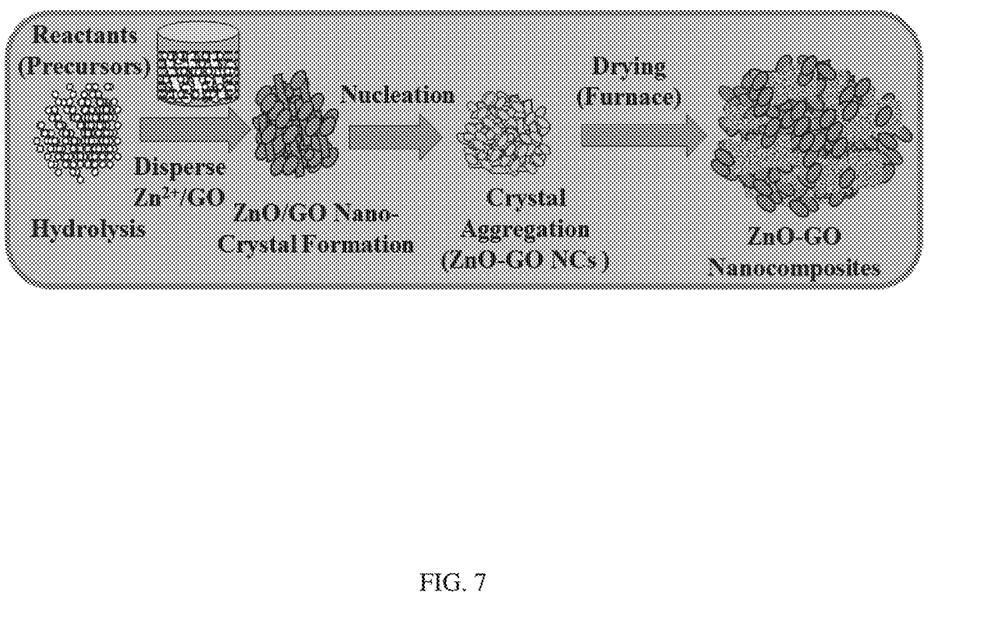
FIG. 7. The nanocomposite growth mechanism of ZnO/GO NCs produced by wet-chemical method at low temperature.

The reactions [(i) to (iv)] above were expected to progress gradually and the pH played a significant role during the formation of ZnO/GO NCs in the reaction system. As ammonium hydroxide was added into the system to the adjust the pH value at 10.5, the ZnCl$_2$ started to be hydrolyzed and Zn(OH)$_2$ was formed according to the reaction (ii) and (iii). Therefore, the ammonium hydroxide played a dual role as the OH$^-$ supplier and the controller of basic atmosphere in the reaction medium. After a while, as the Zn$^{+2}$ and OH$^-$ concentration were increased and reached to an optimum value, the nuclei of Zn(OH)$_2$ started forming, finally leading to the formation of ZnO/GO NCs in the presence of dispersed GO [eqn (iv)]. The formation of nanoparticles is expected to follow the similar growth pattern as described elsewhere [34-36]. The generated composite metal hydroxide crystals were washed with water three times, with ethanol two times and finally with acetone. The synthesized Zn(OH)$_2$/GO was dried at atmospheric conditions overnight, then the calcination was performed at 500° C. for 6 hours using a Barnstead Thermolyne, 6000 Furnace (purchased from USA). The mechanism for the nanocomposite development of ZnO/GO NCs is shown in FIG. 7.

Fabrication of PEDOT:PSS/ZnO/GO NCs/GCE Electrode

Active material for the probe was obtained by making ethanoic slurry of ZnO/GO NCs. The mixture was coated on the top of a GCE and was dried completely at room conditions. To provide the chemical adhesive property between the GCE and ZnO/GO NCs electron mediator, a drop of PEDOT:PSS is dropped. After that, PEDOT:PSS/ ZnO/GO NCs/GCE assembly was dried in an oven at 34.0° C. for 1 hour. Complete drying of the conducting PEDOT: PSS/ZnO/GO NCs/GCE layer was ensured. The PEDOT: PSS/ZnO/GO NCs/GCE as well as 1.5 mm (diameter) Pt-wire were connected with an electrochemical cell. The PEDOT:PSS/ZnO/GO NCs/GCE assembly functioned as WE (working electrode), whereas the round-thin Pt-wire was rolled as a counter electrode. The thickness of fabricated PEDOT:PSS/ZnO/GO NCs film onto flat GCE is 0.5 μm. PHyd analyte solution of varied concentration (within the range of 0.10 nM-1.0 mM) was prepared and was analyzed by using the assembled electrochemical cell. The sensitivity of the PEDOT:PSS/ZnO/GO NCs/GCE working electrode was obtained by calculating the slope of the current vs. concentration plotting. Linear dynamic range (LDR) as well as the detection limit (LOD) were evaluated by calculating the 3N/S ratio (ratio of Noise×3 verses Sensitivity). 0.1 M PBS-buffered system was maintained for the 10.0 mL analyte solution in a beaker during the entire electrochemical sensing experimentation. The devised electrochemical assembly depicts a current-voltage curve, measured by means of the two electrode circuit.

The amount of PEDOT:PSS and ZnO/GO are 1.0 uL and 1.0 ug respectively. Mixture of these two nanocomposites were deposited (at 1:1 ratio) onto GCE electrode.

Results

Characterization of the ZnO/GO Nanocomposite

Figure 1A:
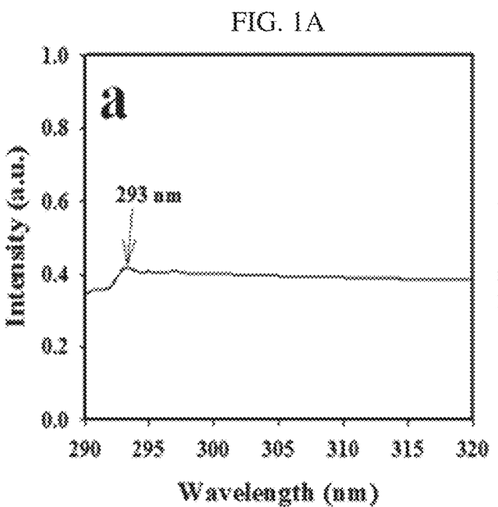
FIGS. 1A-C. Characterization of ZnO/GO NCs. (A) UV-vis. spectra, (B) FTIR, and (C) powder XRD pattern.

The identification of photo-electronic properties of the prepared nanocomposite is a prime and countable criterion. Therefore, the transitional metal oxide composited with nanosheets of graphene oxide (ZnO/GO NCs) were examined by UV-vis spectrum by exposing the sample to visible light. During the absorption of a characteristic wavelength of visible light by the sample, electrons from the filled molecular orbital migrate from a lower energy level to a higher one [37] resulting in the characteristic UV-vis spectrum. For an intensive study, the wavelength was scanned between 400 and 800 nm at ambient conditions. The UV-vis spectrum presented in FIG. 1(a) demonstrated an identical characteristic band with a peak at 293 nm. The obtained UV absorption band is authentication for the migration of electrons from the lower occupied molecular orbital to the higher energy empty band of ZnO/GO NCs molecular orbital system. Therefore, the UV-vis spectrum results in the computed optical band gap ($E_{bg}$), as 4.23 eV obtained from the relation $E_{bnd\ gp}=1240/\lambda_{max}$, where, $E_{bnd\ gp}$ is the energy difference associated with the band-gap and $\lambda_{max}$ is the wavelength undergoing the maximum absorption [38-41].

Figure 1B:
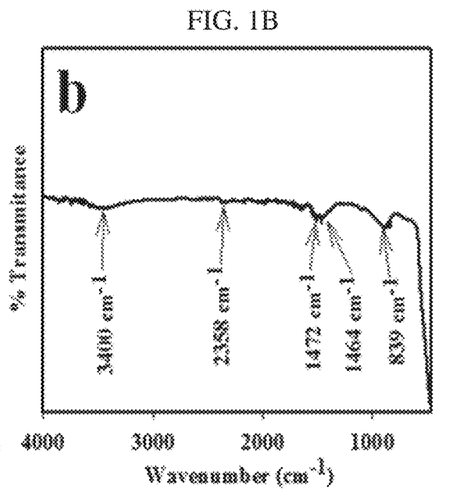

FTIR (Fourier-transform infrared spectroscopy) was considered as another important specification tool for identification of functional groups of the prepared nanocomposite. The response in FTIR was raised from the corresponding molecular vibration of nanomaterials during the IR radiation exposure. In fact, the FTIR is an authentic tool for characterization, and it was operated at the range of 450-4000 cm$^{-1}$ for our synthesized sample at ambient condition. The spectrum revealed in FIG. 1(b) reveal several peaks at 839, 1464, 1472, 2358, and 3400 cm$^{-1}$. The presence of the sharp and majorly visible peak at 1464 and 1472 cm-$^1$ can be recognized for the presence of H—O—H (available due to the adsorption of moisture) bending vibration mode, [42]. The peak at 3400 cm$^{-1}$ arises from the O—H stretching vibration [43, 44] and the peak at 839 cm$^{-1}$ was responsible for the vibration mode of C—O groups [45] and the C=O carbonyl stretching was at 2358 cm$^{-1}$ [46, 47] respectively.

Figure 1C:
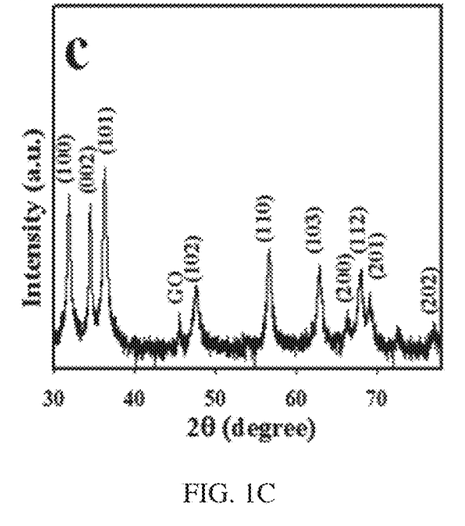

The phase (crystallinity) and purity of synthesized nanocomposite of ZnO/GO are other important qualitative parameters of the samples. This information can depict the details about structure and unit cell pattern of the samples. Therefore, the resultant ZnO/GO NCs were studied further using the Powder XRD facility. The XRD facility includes an energy radiant Cu-K1(=1.54178A°) within a usual range (10-80.) with of 2° per min scanning speed. In FIG. 1(c), the indistinguishable peaks of ZnO are displayed in the measured XRD spectra and confirm that the synthesized ZnO/ GO NCs contains well-defined phases associated with ZnO and GO. ZnO displays the reflection peaks as (002), (100), (101), (102), (103), (110), (112), (200), (201) and (202) and matches completely with some previous reports on the XRD pattern of ZnO [48-51]. In addition, the ZnO decorated on the GO sheets as hexagonal phase [52] was confirmed by the JCPDS No. 36-1451 as implicated by equation (v).

$$D=0.9\lambda/(\beta\cos\theta) \qquad (v)$$

Here, $\lambda$, $\beta$ and $\theta$ represent the X-ray radiation wavelength (1.5418 Å), the half value of width at the height of the peak with maximum intensity and the angle of diffraction, respectively [53].

Figure 2A:
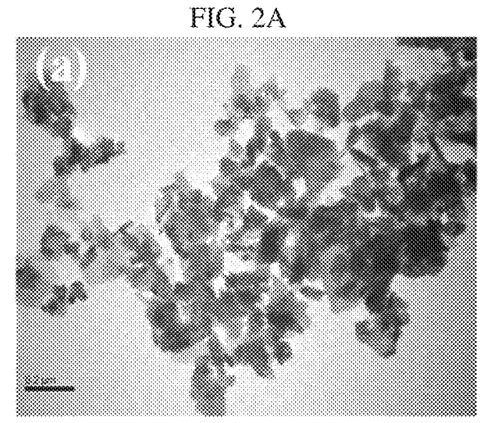
FIGS. 2A-C. (A) First, (B) second, and (C) third TEM images of ZnO/GO nanocomposites.
Figure 2B:
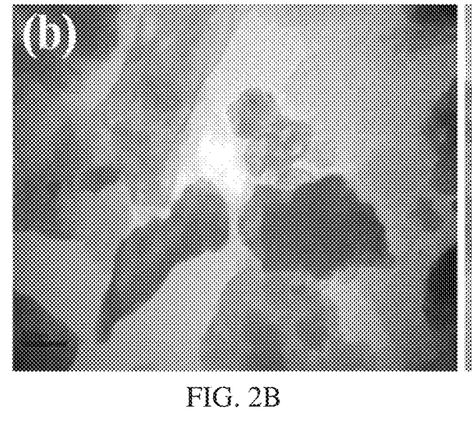
Figure 2C:
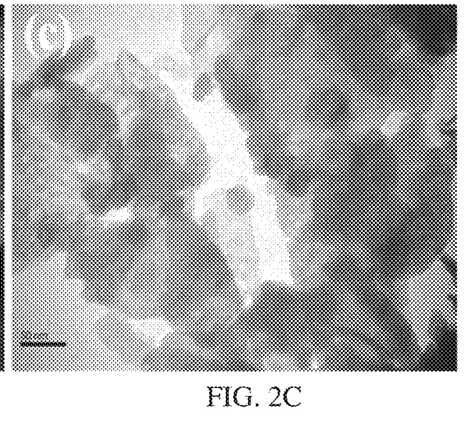

The encapsulation of ZnO nanoparticles on flat GO nanosheet was confirmed from morphology survey by means of TEM analysis. The TEM image of ZnO/GO NCs in FIG. 2 reveals that the aggregated spherical-shaped particle-like denser spots of ZnO nanoparticles are dispersed on GO. The dimensions of ZnO nanoparticles were found to be 7.9 nm in an average within the range of 6.0-10.0 nm. The aggregated ZnO nanoparticles on the surface of GO (FIG. 2a-c) seem to grow randomly and the nanocomposites appear to be generated from the adsorption of ZnO precursor on GO with a prerequisite condition of nucleation. The TEM images display the deposition of nanocomposites on the GO. The random dispersion of denser spots indicates the seeding and gradual growth of the seeds as the possible route for the generation of ZnO-encapsulated GO.

Figure 3A:
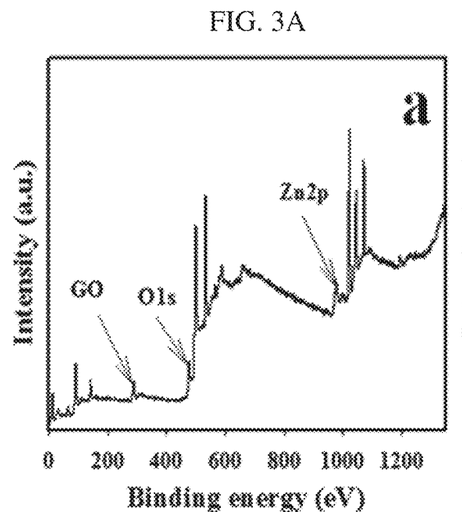
FIGS. 3A-D. XPS spectra of of ZnO/GO NCs. (A) Full-range spectrum, (B) O1s spectra, (C) Spin-orbit level Zn3d, and (D) Spin-orbit level of C1s.
Figure 3B:
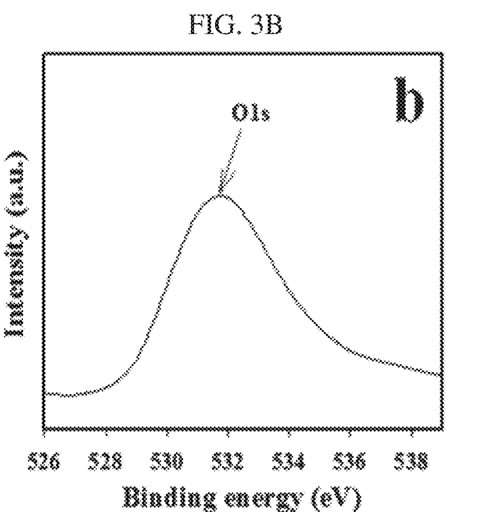
Figure 3C:
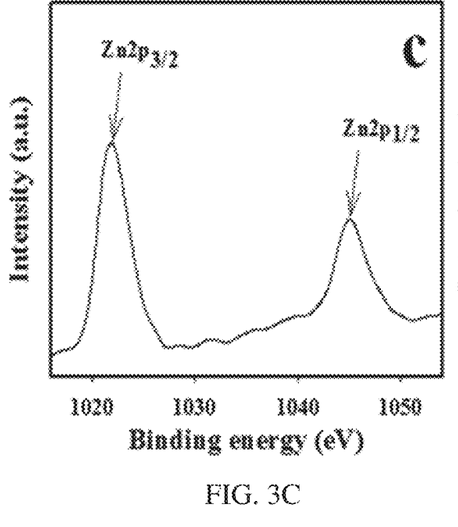
Figure 3D:
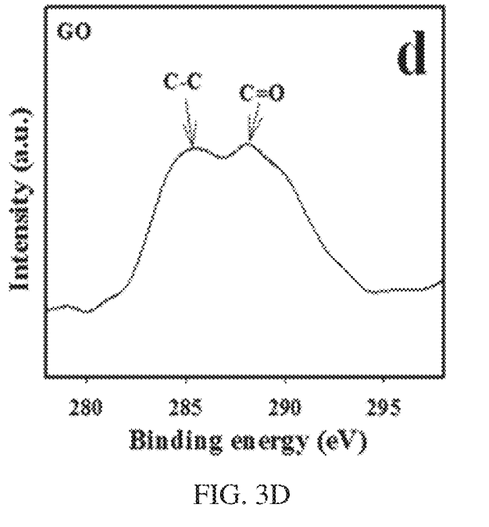

XPS (X-ray photoelectron spectroscopy) is a significant and highly efficient technique for detecting the chemical bond and binding energy of individual elements in nanocomposites. XPS can precisely measure the elemental composition of the surface, chemical bonding and electronic configuration of the component elements that exist in the composite material. Hence, the chemical bonding and the oxidation states of respective chemical species in the synthesized ZnO/GO NCs were determined using XPS. During the XPS study, the energy of the radiant X-ray photon interacts with the material and stimulates the electrons in the spin-orbital of the synthesized nanocomposite. The electrons thus become excited and migrate from the lower energy level to the higher one resulting in the particular XPS spectrum. Hence, the chemical formula, atomic composition and oxidation state of component elements present in any material may be analyzed efficiently by employing XPS analysis [54, 55]. The XPS pattern of ZnO/GO NCs shown in FIG. 3 confirms the presence of O, Zn, and GO distinctly. Two identical peaks for Zn2p orbital in the sample ZnO/GO NCs remains reproducible over several measurements. There was no apparent change between these twin peaks and they indicate the similar oxidation state of Zn precursor in the sample. The observed binding energies as 1022 and 1045 eV corresponds to the $Zn2p_{3/2}$ and $Zn2p_{1/2}$ electronic state. The resultant binding energy ($E_{bg}$) difference of these two oxidation states of Zn, as 23 eV are characteristic for the oxidation of $Zn^{2+}$ in ZnO (FIG. 3(c)) [56-60]. In FIG. 3(b), the peak at 532 eV is associated with the oxygen precursor attached to the surface oxide groups of ZnO [61-65]. In FIG. 3(d), the characteristic XPS spectra of GO (Cis) appear at 288 and 285 eV. These two peaks are assigned to the C═O and C—C bonds, respectively [66-68].

Phenylhydrazine Detection with PEDOT:PSS/ZnO/GO NCs/GCE Electrode

Figure 8:
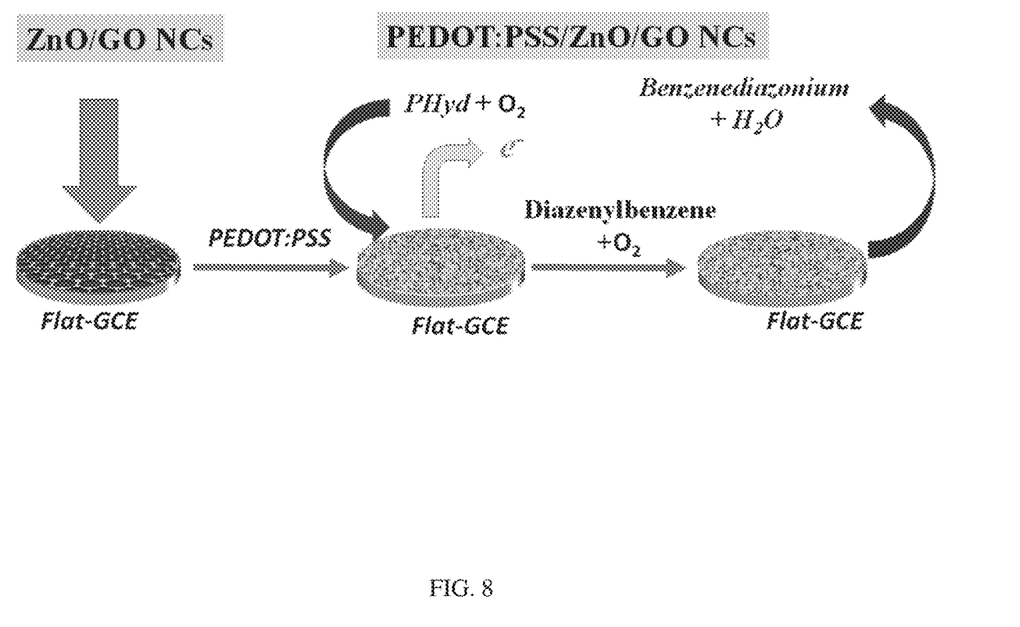
FIG. 8. Mechanism for oxidative quantification of phenyl hydrazine by PEDOT:PSS/ZnO/GO NCs/GCE probe according to an embodiment of the disclosure.

We applied the PEDOT:PSS/ZnO/GO NCs/GCE probe as a working probe for detecting target PHyd toxin as the analyte in buffer solution. The electrochemical sensor has outstanding benefits such as chemical inertness, physicochemical stability, improved electrochemical efficiency, ease of operation, assembling and fabrication and safe chemocharacteristic. The devised PHyd probe was applied to detect PHyd of varied concentrations in buffer system and PEDOT:PSS/ZnO/GO NCs based GCE probe successively worked with excellent efficiency during the sensing operation. To devise the PHyd electrochemical sensor, top of GCE was modified by attaching a slurry of ZnO/GO NCs followed by a complete drying at ambient temperature. Binding between the ZnO/GO NCs thin-film and GCE-top was stabilized by using conducting polymer PEDOT:PSS mixtures as the chemical agent. After applying PEDOT:PSS, the electrode was kept at 34° C. until the conducting binder was dried thoroughly. During the sensing experiment, the displayed current against scanned potential (I-V) was detected using the PEDOT:PSS/ZnO/GO NCs/GCE as the working probe. The electrochemical response was found to be increased markedly as PHyd molecules becomes adsorbed from the aqueous solution to the PEDOT:PSS/ZnO/GO NCs/GCE surface during the electrochemical mood of oxidation. The holding period was set (in the electrometer) to be 1.0 sec. The current at a certain voltage is generated from the electrochemical oxidation process, respective chemical reactions for which are presented by equations (vi) to (ix). The possible mechanism for the oxidation of PHyd is illustrated in FIG. 8. According to this mechanism, increasing the electron numbers in analyte solution resulted in the sensing of target analyte by sensor probe in this experiment. The electron becomes mediated by the GO counterpart and the increase in current becomes displayed. As it was stated in reaction (vi), the active oxygen precursors become attached on PEDOT:PSS/ZnO/GO NCs/GCE surface and the conduction electrons being eliminated enhances the resistance of reaction medium.

According to the reaction (vii), the adsorbed PHyd on PEDOT:PSS/ZnO/GO NCs/GCE surface reacts with oxygen ion (O⁻) and becomes transformed into diazenyl benzene and more free electrons [69, 70]. The produced diazenylbenzene further becomes oxidized to benzenediazonium as illustrated in reaction (ix) [71]. This series of electrochemical conversions causes an increase in electrochemical response during the sensing of of PHyd. FIG. 8 depicts the consecutive transformation of PHyd.

$$e^{-}(ZnO/GO) + O_2 \rightarrow 2O^{-} \quad \text{(vi)}$$

$$PHyd + O^{-} \rightarrow \text{Diazenyl Benzene} + H^{+} + OH^{-} + e \quad \text{(vii)}$$

$$H^{+} + OH^{-} \rightarrow H_2O \quad \text{(viii)}$$

$$\text{Diazenyl Benzene} + \frac{1}{2}O_2 + H^{+} \rightarrow \text{Benzenediazonium} + H_2O \quad \text{(ix)}$$

Figure 4A:
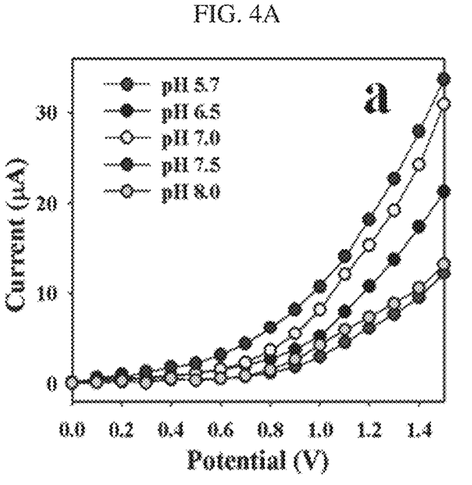
FIGS. 4A-D. Justification of PHyd sensor using PEDOT:PSS/ZnO/GO NCs/GCE electrode. (A) pH variation, (B) test for selectivity, (C) repeatable stage and (D) time of response.
Figure 4B:
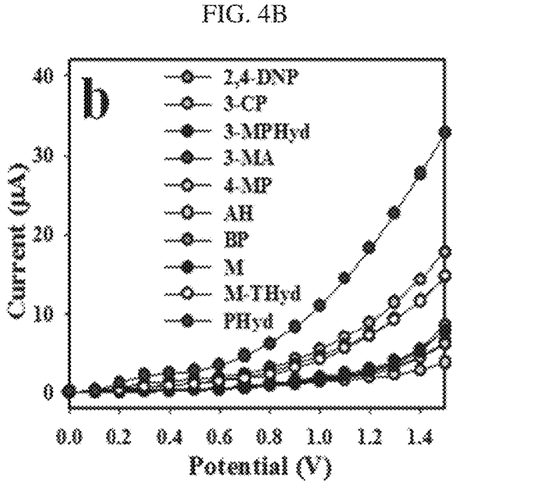
Figure 4C:
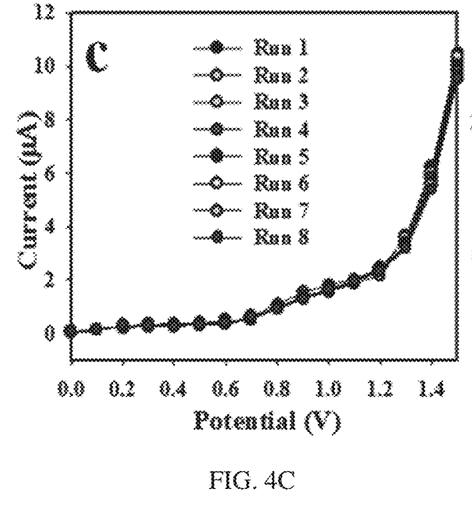
Figure 4D:
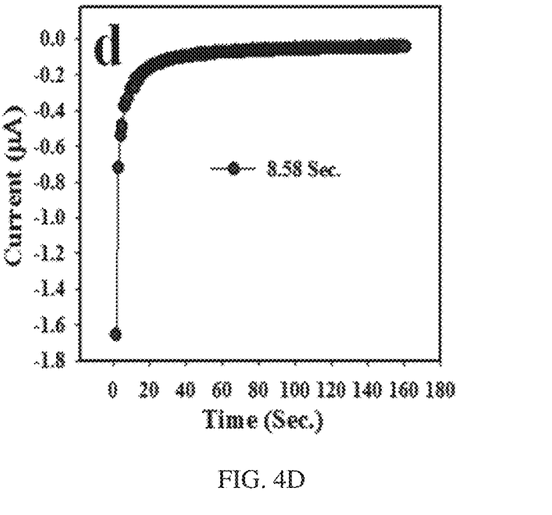

The devised PEDOT:PSS/ZnO/GO NCs/GCE electrode was not found to exhibit equal response in all the possible buffer states. To find the optimized buffer system, PEDOT:PSS/ZnO/GO NCs/GCE (working electrode) assembly was tested in buffers stabilizing various specific pH (i.e. pH=5.7, 6.5, 7.0, 7.5 and 8.0) (FIG. 4a). A pH of 7.5 was found to reveal the optimized response and sensitivity toward PHyd detection. The electrochemical measurements were carried out by the implementation of the Keithley electrometer, where the applied electrical potential was adjusted in the range of 0 to +1.5 V. The environmental toxin including PHyd, 3-MPHyd, 3-CP, 2,4-DNP, M-THyd, 4-MP, AH, 3-MA, BPA and methanol were tested with the fabricated working electrode. Respective I-V curves in FIG. 4(b) show that PHyd exhibits the maximum current response. The reproducibility of the proposed chemical sensor was justified by measuring the current response for 0.1 μM PHyd. The respective result is demonstrated in FIG. 4(c). Excellent reproducible signals were observed and the electrochemical signals were unchanged despite the PEDOT:PSS/ZnO/GO NCs/GCE probe being cleaned prior to all the unit tests. The reproducibility's standard-deviation (RSD) was measured and it was 3.17% at +0.5V. The response time being another important parameter for evaluating the sensing efficiency, was tested by using an analyte of 0.1 μM PHyd solution. An excellent response time of 8.58 seconds as presented in FIG. 4(d) was obtained.

Figure 5A:
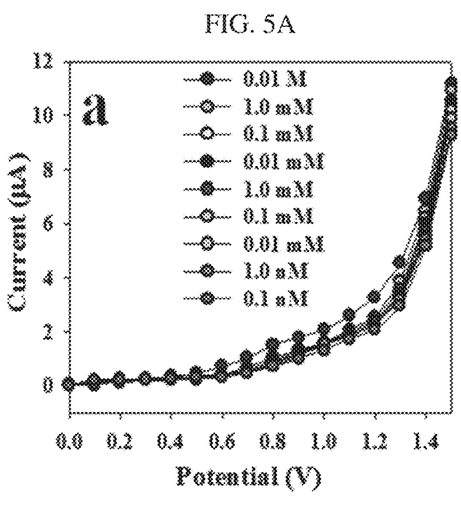
FIGS. 5A-C. Study of electrochemical performance of PEDOT:PSS/ZnO/GO NCs/GCE electrode at varied concentrations of Phyd. (A) I-V curve displayed at various concentrations, (b) amplified concentration variation and (c) curve for calibration (Inset: log [PHyd. Conc.] with respect to current).
Figure 5B:
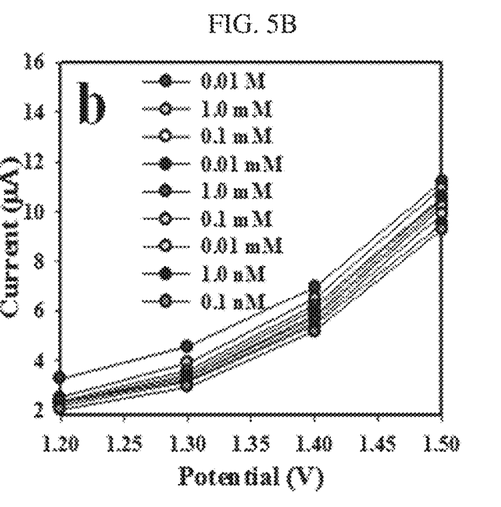
Figure 5C:
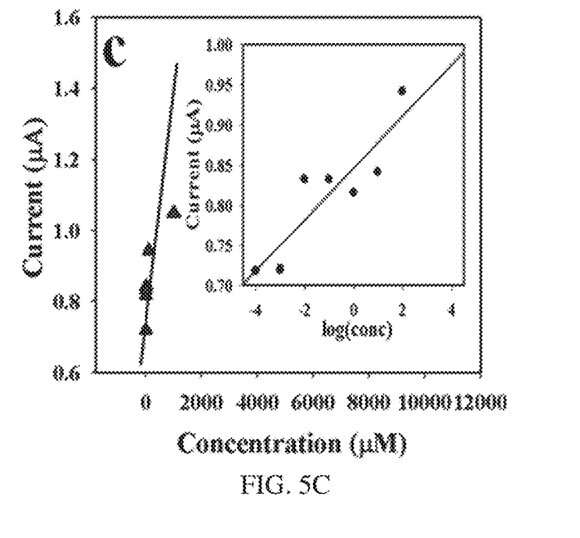

We measured the current vs voltage responses of the working electrode at varied PHyd concentrations. The electrochemical response displayed direct proportionality with respect to the concentration of PHyd. Also, we found that with the enrichment of PHyd concentration, electrochemical response increases rapidly. A range of PHyd solutions having various concentrations within 0.1 nM to 0.01 M was examined with a positive scanning of potential within the range of 0 to +1.5 V. The respective results are shown in FIG. 5(a) and is magnified in FIG. 5(b). In performance computation of PHyd electrochemical sensor, the linearity ($r^2$=0.9907) of the plot was evaluated at +0.8 V (FIG. 5(c)). The sensitivity (43.82 μAmM$^{-1}$cm$^{-2}$) of the PEDOT:PSS/ZnO/GO NCs/GCE probe was obtained from the ratio of current vs concentration curve. Linear Dynamic Ranges (LDR: 0.1 nM to 1.0 mM) as well as the limit of detection (LOD: 0.022 nM) have been determined from the calibration curve considering the ratio between signal and noise as 3. The limit of quantification (LOQ) is also calculated as 0.073 Nm.

In all quantitative detection experimentation of PHyd, the applied current signal against the scanned potential remained linearly proportional with respect to the concentration of PHyd. The similar tendency of I-V curves with respect to the concentration of analyte was reported in some previous literature [71-74]. At the starting of PHyd sensing, an inferior number of PHyd molecules become adsorbed on the PEDOT:PSS/ZnO/GO NCs/GCE film and the oxidation process initiates. The oxidation reaction increases gradually with increasing analyte (PHyd) concentration as a gradually larger surface is covered by PHyd molecules at a higher concentration of the analyte. As a continuation of the process, further enrichment of the PHyd concentration results in higher surface coverage and a multiplied electrochemical signal is noticed. In fact, occupying the surface of PEDOT:PSS/ZnO/GO NCs/GCE working electrode by PHyd plays a crucial role in the oxidative signal generation. Due to the farther increase in analyte concentration on the probe surface, the surface adherence by PHyd entity reaches to the point of saturation and the multiplied I-V response is observed. Therefore, it can be concluded that the PEDOT:PSS/ZnO/GO NCs/GCE fabricated PHyd chemical sensor can efficiently be used for the detection of PHyd. As we found that the devised PHyd chemical sensor exhibited a response time of 8 sec, it is clear that reaching to the steady state saturation needs 8 seconds minimum. The developed PHyd sensor demonstrating a moderately high sensitivity of 43.8169 $\mu AmM^{-1}cm^{-2}$, might demand that it possess improved functionality toward catalytic decomposition of PHyd molecules, high adsorption capacity and biocompatibility [75-78]. Fulfilling these general accreditation measures of an electrochemical sensor, the devised PHyd sensor can be classified as a high performing quantitative electrochemical sensor for PHyd. A comparison of the sensing performance parameters including LD, LDR and extent of sensing of the newly devised PHyd sensor with some previously reported ones are illustrated in Table. 1. [31, 32, 71, 79, 80, 81]. As ZnO/GO NCs ensure high crystallinity and enhanced electron mediation property, the devised sensor provides a satisfactory performance in all respect. No doubt, the fabricated electrochemical sensor for PHyd is a simple, affordable and sophisticated means to quantify PHyd by means of current versus voltage study approaches.

TABLE 1

Comparison of performance of the newly developed PHyd sensors with different fabricated electrodes reported elsewhere.

| Electrode Assembly | DL | LDR | Sensitivity | Ref |
|---|---|---|---|---|
| ZnO NCs/GCE | 78.6 µM | — | 42.1 µAcm$^{-2}$mM$^{-1}$ | 31 |
| TiO$_2$ NTs/GCE | 0.22 µM | — | 40.9 µAcm$^{-2}$mM$^{-1}$ | 32 |
| ZnO-Fe$_2$O$_3$ Ws/AuE | 0.67 nM | 1.0 nM-10.0 mM | 8.33 µAcm$^{-2}$mM$^{-1}$ | 71 |
| Glassy carbon electrode | 0.05 µM | 2.0-20.0 µM | 16.0 µAmM$^{-1}$ | 79 |
| Carbon Paste Electrode | 40.0 nM | 7.0 × 10$^{-8}$-9.0 × 10$^{-4}$M | 16.0 µA · mM-1 | 80 |
| V$_2$O$_5$/ZnO NCs (NCs) | 0.09631 nM | 0.01 mM-0.1 nM | 12.389 µAµM$^{-1}$cm$^{-2}$ | [81] |
| PEDOT:PSS/ZnO/GONCs/GCE | 0.022 nM | 0.1 nM-0.1 mM | 43.82 µAcm$^{-2}$mM$^{-1}$ | Present Task |

* DL = Limit of Detection, LDR = Linear Dynamic Detection Range, nM = Nanomole

Figure 6A:
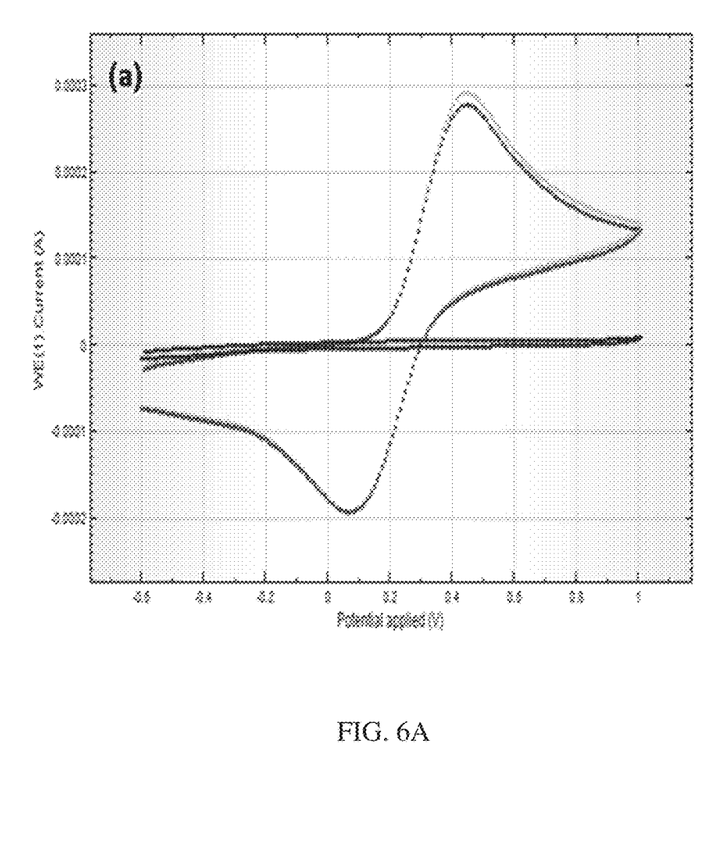
FIGS. 6A-B. Electrochemical characterization of PEDOT:PSS/ZnO/GO NCs/GCE. Comparison of (A) Cyclic voltammetry of (B) Nyquist plots (EIS) of PEDOT:PSS/ZnO/GCE, PEDOT:PSS/GO/GCE, and PEDOT:PSS/ZnO/GO NCs/GCE at pH=7.0 in 0.1 M PBS.

Finally, for electrochemical characterization of PEDOT:PSS/ZnO/GO NCs/GCE electrode, it was electrochemical characterized with conventional cyclic voltammetry (CV) as well as electrochemical impedance spectroscopy (EIS) methods. The electrochemical redox and impedance properties of PEDOT:PSS/ZnO/GCE, PEDOT:PSS/GO/GCE, PEDOT:PSS/ZnO/GO NCs/GCE sensor probes is elaborately characterized here for the efficient analyte detection by electrochemical approach. For the fabricated electrode characterization purpose, at first, GCE was fabricated by immobilizing separately with only ZnO, GO, and ZnO/GO NCs with the help of conducting polymer PEDOT:PSS binder. Here, three electrode systems were used in electrochemical analysis, where Ag/AgCl (Sat. KCl), PEDOT:PSS/ZnO/GO NCs/GCE, and Pt was used as reference, working and counter electrode respectively. The results of cyclic voltammetric (CV) response in ferricyanide redox couple [Fe(CN)$_6$]$^{3-/4-}$) are investigated and shown in FIG. 6a. Here, the electron transfer activity is measured within the ZnO/GCE, GO/GCE and PEDOT:PSS/ZnO/GO NCs/GCE by CV method in 5.0 mM [Fe(CN)$_6$]$^{3-/4-}$ solution (FIG. 6a). The PEDOT:PSS/ZnO/GO NCs/GCE exhibited good oxidation and reduction peaks at +0.42V and +0.11V respectively.

Figure 6B:
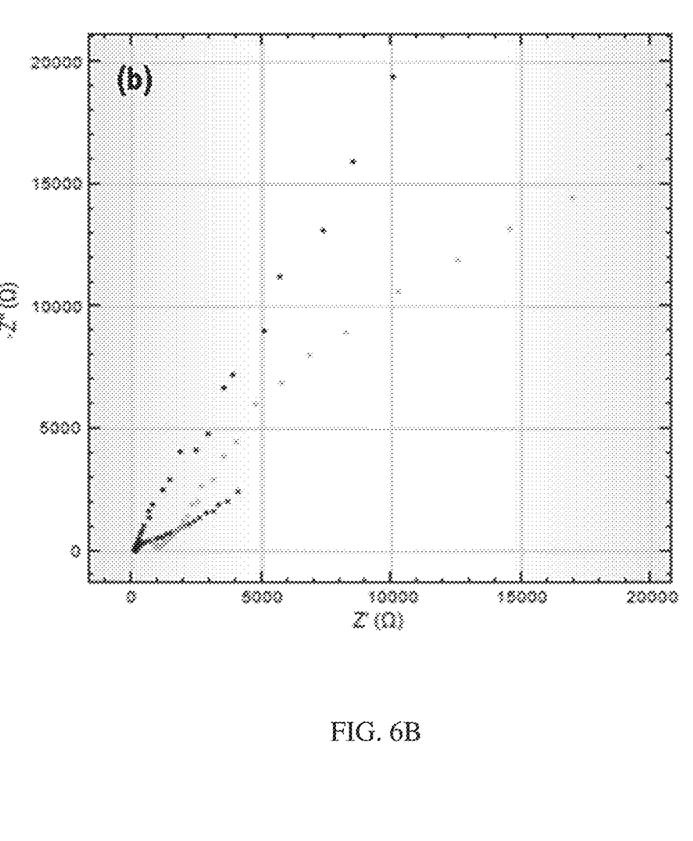

However, PEDOT:PSS/ZnO/GCE and PEDOT:PSS/GO/GCE are also exhibited slight response in the identical measurement compared to PEDOT:PSS/ZnO/GO NCs/GCE. This indicates that PEDOT:PSS/ZnO/GO NCs/GCE significantly improved the electron transfer ability of the GCE [82]. This is confirmed by the results obtained in CV, where PEDOT:PSS/ZnO/GO NCs/GCE exhibited the highest conductance as compared to PEDOT:PSS/ZnO/GCE and PEDOT:PSS/GO/GCE. In this approach, EIS is very useful in evaluating electron mobility on the electrode-solution interface and resistivity of prepared ZnO/GO NCs towards the current. Therefore, an EIS investigation was carried out to further confirm the electrochemical characterization of PEDOT:PSS/ZnO/GCE and PEDOT:PSS/GO/GCE as well as coated PEDOT:PSS/ZnO/GO NCs/GCE electrode. A faster electron mobility on the PEDOT:PSS/ZnO/GO NCs/GCE was expected if the fabrication of PEDOT:PSS/ZnO/GO NCs onto GCE was successful. In EIS, the diameter of the semicircle denotes the charge-transfer resistance (RCT) at the surface of the PEDOT:PSS/ZnO/GO NCs/GCE [83]. As presented in FIG. 6b, the PEDOT:PSS/ZnO/GCE and PEDOT:PSS/GO/GCE electrodes displayed a higher resistance compared to the PEDOT:PSS/ZnO/GO NCs/GCE in a solution containing 5.0 mM ferricyanide (0.1M PBS; pH at 7.0). This shows that PEDOT:PSS/ZnO/GO NCs/GCE has enhanced the charge-transfer ability of the NCs-modified sensor probe surface. This is also an indication that the conductivity of the modified-GCE has greatly increased due to enhanced electron transfer properties of fabricated ZnO/GO NCs with GCE [84]. The complex plane plots displayed in FIG. 6b indicates that in 0.1 M PBS/K$_3$[Fe(CN)$_6$], the PEDOT:PSS/ZnO/GO NCs/GCE exhibited less capacitive current as well as lower impedance (R$_{CT}$: 956Ω) compared to the PEDOT:PSS/ZnO/GCE and PEDOT:PSS/GO/GCE electrodes. The less capacitive nature with less impedance of the PEDOT:PSS/ZnO/GO NCs/GCE sensor suggests the electron-transfer ability of the PEDOT:PSS/ZnO/GO NCs/GCE electrode was improved in the presence of ZnO/GO NCs coating, while the NC materials were bonded with PEDOT:PSS onto the surface of GCE. Thus, such NCs-modified electro-active property of the GCE suggests that PEDOT:PSS/ZnO/GO NCs/GCE sensor probe enhanced the electrochemical process during EIS observation (FIG. 6b).

Analysis of Real Samples by the PEDOT:PSS/ZnO/GO NCs/GCE Electrode

For sensor validation, the PEDOT:PSS/ZnO/GO NCs/GCE probe was assayed to determine PHyd in the real environmental and extracted samples. We measured PHyd in various environmental and extracted analyte specimens such effluent from industries, PVC based food-packaging, extract of plastic baby bottles, plastic water-bottles, and seawater. The results revealed that the detection of PHyd is satisfactory and the efficiency is in the acceptable ranges. The calculated sensor results are presented in Table 2.

TABLE 2

Real sample analyses with PEDOT:PSS/ZnO/GO NCs/GCE sensor probe by electrochemical approach

| Real Specimen | Current signal(µA) | | | | Av-erage | Conc. (µM) calculated | % RSD |
|---|---|---|---|---|---|---|---|
| | R1 | R2 | R3 | R4 | | | |
| Industrial effluents | 3.18 | 3.31 | 3.37 | 3.59 | 3.3625 | 28.01635 | 5.09 |
| PC baby-bottle | 4.53 | 4.63 | 4.82 | 5.44 | 4.8550 | 40.45186 | 8.41 |
| Safa water-battle | 3.65 | 3.72 | 3.71 | 3.81 | 3.7225 | 31.01587 | 1.77 |
| PVC food packaging-bag | 2.32 | 2.30 | 2.28 | 2.35 | 2.3125 | 19.26775 | 1.29 |
| Sea Water | 6.27 | 6.67 | 6.92 | 7.48 | 6.8350 | 56.94922 | 7.41 |

*R = reading, RSD = Relative standard deviation

The following steps may be performed to develop the desired PEDOT:PSS/ZnO/GO NCs/GCE electrode for the detection of carcinogenic PHyd chemical by electrochemical I-V approach:

- pH is optimized with PEDOT:PSS/ZnO/GO NCs/GCE electrode in various pH ranges.
- Selectivity is done in presence of common interfering toxic chemicals as well as with other unsafe chemicals with PEDOT:PSS/ZnO/GO NCs/GCE electrode by electrochemical method.
- The sensor-to-sensor and run-to-run repeatability for PHyd detection is measured using PEDOT:PSS/ZnO/GO NCs/GCE electrode.
- Electrode response time is measured from the facile and easy I-V method with PEDOT:PSS/ZnO/GO NCs/GCE electrode.
- Significant effect of current changes is determined by injecting various concentrations of PHyd from low to high concentration with PEDOT:PSS/ZnO/GO NCs/GCE electrode.
- A calibration plot is drawn from the concentration of PHyd analytes and the analytical parameters of PEDOT:PSS/ZnO/GO NCs/GCE electrode performances are calculated.
- A control experiment is performed with different modifications of only ZnO, GO, ZnO/GO with PEDOT:PSS conducting polymer in presence of common ferrocyanide couples.

REFERENCES

[1] A. Ibrahim, G. N. Dar, S. A. Zaidi, A. Umar, M. Abaker, H. Bouzid, S. Baskoutas. Talanta. 93 (2012) 257-263.
[2] I. Tiwari, M. Gupta, P. Sinha, S. K. Aggarwal. Electrochimica Acta. 76 (2012): 106-111.
[3] A. Umar, M. M. Rahman, S H Kim, Y. B. Hahn. Chemical Communications. 2 (2008) 166-168.
[4] S. Shukla, S. Chaudhary, A. Umar, G. R. Chaudhary, S. K. Mehta. Sensors and Actuators B: Chemical. 196 (2014) 231-237.
[5] I. Tiwari, M. Gupta, P. Sinha, S. K. Aggarwal. Electrochimica Acta. 76 (2012) 106-111.
[6] A. Abbaspour, M. Shamsipur, A. Siroueinejad, R. Kia, P. R. Raithby. Electrochimica Acta. 54.10 (2009) 2916-2923.
[7] J. W. Mo, B. Ogorevc, X. Zhang, B. Pihlar. Electroanalysis. 12 (2000) 48-54.
[8] H. R. Zare, N. Nasirizadeh, F. Chatraei, S. Makarem. Electrochimica Acta. 54 (2009) 2828-2836.
[9] S. D. Zelnick, D. R Mattie, P. C. Stepaniak. Avait. Space Environ. Med. 74 (2003) 892.
[10] S. Garrod, M. E. Bollard, A. W. Nicholls, S. C. Connor, J. Connelly, J. K. Nicholson, E. Holmes. Chemical research in toxicology. 18 (2005) 115-122.
[11] K. Yamada, K. Yasuda, N. Fujiwara, Z. Siroma, H. Tanaka, Y. Miyazaki, T. Kobayashi. Electrochemistry communications. 5 (2003): 892-896.
[12] N. Rastakhiz, A. Kariminik, V. S. Nejad, S. Roodsaz. Int. J. Electrochem. Sci. 5(2010), 1203-1212.
[13] M. George, K. S. Nagaraja, N. Balasubramanian. Talanta. 75 (2008) 27
[14] M. A. Chamjangali, G. Bagherian, S. Ameri. Journal of hazardous materials. 166 (2009) 701-705.
[15] W. Siangproh, O. Chailapakul, R. Laocharoensuk, J. Wang. Talanta. 67 (2005) 903-907.
[16] M. Mori, K. Tanaka, Q. Xu, M. Ikedo, H. Taoda, W. Hu. Journal of Chromatography A. 1039(2004) 135-139.
[17] A. Safavi, M. A. Karimi. Talanta. 58 (2002) 785-792.
[18] D. Afzali, H. K. Maleh, M. A. Khalilzadeh. Environ. Chem. Lett. 9 (2011) 375-381.
[19] S. W. Hwang, A. Umar, G. N. Dar, S. H. Kim, R. I. Badran. Sensor Lett. 12 (2014) 97-101.
[20] R. J. Wu, J. G. Wu, M. R. Yu, T. K. Tsai, C. T. Yeh. Sensors Actuators B Chem. 131 (2008) 306-312.
[21] B. Zhao, G. Shao, B. Fan, W. Li, X. Pian, R. Zhang. Mater. Lett. 121 (2014) 118-121.
[22] M. Yin, S. Liu. Sensors Actuators B Chem. 197 (2014) 58-65.
[23] M. M. Rahman, H M Marwani, F. K. Algethami, A. M. Asiri. New J. Chemistry 41 (2017) 6262-6271.
[24] S. K. Lim, S. H. Hwang, D. Chang, S. Kim Sensors Actuators B Chem. 149 (2010) 28-33.
[25] Hafeezullah, Z. H. Yamani, J. Iqbal, A. Qurashi, A. Hakeem. J. Alloys Compd. 616 (2014) 76-80.
[26] S. T. Navale, G. D. Khuspe, M. A. Chougule, V. B. Patil. Org. Electron. 15 (2014) 2159-2167.
[27] B. Geng, F. Zhan, C. Fang, N. Yu. J. Mater. Chem. 18 (2008) 4977-4984.
[28] E. Sennik, N. Kilinc, Z. Z. Ozturk. J. Alloys Compd. 616 (2014) 89-96.
[29] T. Xiao, X. Y. Wang, Z. H. Zhao, L. Li, L. Zhang, H. C. Yao, J. S. Wang, Z. J. Li. Sensors Actuators B Chem. 199 (2014) 210-219.
[30] M. M. Rahman, G. Gruner, M. S. Al-Ghamdi, M. A. Daous, S. B. Khan, A. M. Asiri. Int. J. Electrochem. Sci. 8 (2013) 520-534.
[31] M. M. Rahman, G. Gruner, M. S. Al-Ghamdi, M. A. Daous, S. B. Khan, A. M. Asiri. Int. J. Electrochem. Sci., 8 (2013) 520-534.
[32] S. Ameen, M. S. Akhtar, H. K. Seo, H. S. Shin. Appl. Phys. Lett. 103 (2013) 061602.
[33] S. Kochmann, T. Hirsch, O. S. Wolfbeis. Tr. AC Trends in Analytical Chemistry. 39 (2012) 87-113.
[34] M. M. Rahman, M. M. Hussain, A. M. Asiri. RSC Adv. 6 (2016) 65338-65348.
[35] M. M. Rahman, J Ahmed, A. M. Asiri, I. A. Siddiquey, M. A. Hasnat. RSC Adv. 6(2016) 90470-90479.
[36] M. M. Hussain, M. M. Rahman, A. M. Asiri. PLoS ONE. 11 (2016) 0166265.
[37] A. A. P. Khan, A. Khan, M. M. Rahman, A. M. Asiri. J. Sol-Gel Sci. Technol. 77 (2016) 361-370.
[38] Y. Haldorai, W. Voit, J. J. Shima. Electrochimica Acta. 120 (2014) 65-72.
[39] S. Yang, W. Yue, D. Huang, C. Chen, H. Lin, X. Yang. RSC Advances. 2 (2012) 8827-8832.
[40] K B Ramirez, C. E. B. Diaz, M. D. I. Herrera, A. L. M. Hernandez, R. N. Rangel, C. V. Santos. Journal of Environmental Health Science & Engineering. 13 (2015) 33.

[41] M. Jana, S. Saha, P. Khanra, N. C. Murmu, S. K. Srivastava, T. Kuila, J. H. Lee. Materials Science and Engineering B. 186 (2014) 33-40.

[42] T. Gutul, E. Rusu, N. Condur, V. Ursaki, E. Goncearenco, P. Vlazan. Beilstein J. Nanotechnol. 5(2014) 402-406.

[43] M. Al-Fandi, R. Oweis, B. A. Albiss, T. AlZoubi, M. A. Al-Akhras, H. Qutaish, H. Khwailah, S. Al-Hattami, E. Al-Shawwa. Materials Science and Engineering. 92 (2015) 012009.

[44] M. Z. Kassaee, E. Motamedi, M. Majdi. Magnetic Fe3O4 graphene oxide/polystyrene:Chemical Engineering Journal. 172 (2011) 540-549.

[45] S. B. Rana, V. K. Bhardwaj, S. Singh, A. Singh, N. Kaur. Journal of Experimental Nanoscience. 9 (2014) 877-891.

[46] A. R. Chowdhuri, S. Tripathy, S. Chandra, S. Roy, S. K. Sahu. RSC Adv. 5 (2015) 49420-49428.

[47] H. Zhang, D. Hines, D. L. Akins. Dalton Trans. 43(2014) 2670-2675.

[48] S. Xua, L. Fub, T. S. H. Pham, A. Yub, F. Hanc, L. Chena. Ceramics International. 141 (2015) 4007-4013.

[49] B. Thangaraj, S. Piraman. Biofuels. 7(2016) 13-20.

[50] V. Eskizeybek, F. San, H. Gulce, A. Gulce, A. Am. Applied Catalysis B: Environmental. 119 (2012) 197-206.

[51] M. Negandary, A. Asadi, S. Mehrtashfar, M. Imandar, H. A. dastjerdi, F. Salahi, A. Jamaleddini, M. Ajdary. Int. J. Electrochem. Sci. 7 (2012) 5185-5194.

[52] F. T. Johra, J. W. Lee, W. G. Jung. J. Indust. Enginnering Chem. 20 (2014) 2883-2887.

[53] R. Jenkins, R. L. Snyder. John Wiley & Sons. 138 (1994) 750-950.

[54] Y. Wang, H. Zhang, D. Yao, J. Pu, Y. Zhang, X. Gao, Y, Sun. J. Solid State Electrochem. 17 (2013) 881-887.

[55] L. Chen, Z. Xu, J. Li, B. Zhou, M. Shan, Y. Li, L. Liu, B. Li, J. Niu. RSC Adv. 4 (2014) 1025-1031.

[56] F. C. Chiu, W. P. Chiang. Materials. 8 (2015) 5795-5805.

[57] N. Gogurla, A. K. Sinha, S. Santra, S. Manna, S. K. Ray. Scientific Reports. 4 (2014) 6483.

[58] Z. Xiong, M. Zheng, C. Zhu, B. Zhang, L. Ma, W. Shen. Nanoscale Research Letters. 8 (2013) 334.

[59] F. Fan, P. Tang, Y. Wang, Y. Feng, A. Chen, R. Luo, D. Li. Sensors and Actuators B. 215 (2015) 231-240.

[60] D. Xu, D. Fan, W. Shen. Nanoscale Research Letters. 8 (2013) 46.

[61] Y. P. Zhu, J. Li, T. Y. Ma, Y. P. Liu, G. Du, Z. Y. Yuan. J. Mater. Chem. A. 2 (2014) 1093-1101.

[62] S. Agnihotri, G. Bajaj, S. Mukherji, S. Mukherji. Nanoscale. 7 (2015) 7415.

[63] F. C. Chiu, W. P. Chiang. Materials. 8 (2015) 5795-5805.

[64] J. Zhang, D. Gao, G. Yang, J. Zhang, Z. Shi, Z. Zhang, Z. Zhu, D. Xue. Nanoscale Research Letters. 6 (2011) 587.

[65] S. Sinha, S. K. Sarkar. RSC Adv. 4 (2014) 47177-47183.

[66] T. Sun, Z. Zhang, J. Xiao, C. Chen, F. Xiao, S. Wang, Y. Liu. Scientific Reports. 3 (2013) 2527.

[67] L. Chen, Z. Xu, J. Li, B. Zhou, M. Shan, Y. Li, L. Liu, B. Li, J. Niu. RSC Adv. 4 (2014) 1025-1031.

[68] A. Y. Romanchuk, A. S. Slesarev, S. N. Kalmykov, D. V. Kosynkinz, J. M. Tour. Phys. Chem. Chem. Phys. 15 (2013) 2321-2327.

[69] A. Umar, M. S. Akhtar, A. Al-Hajry, M. S. Al-Assiri, G. N. Dar, M. S. Islam. Chemical Engineering Journal. 262 (2015) 588-596.

[70] R. Wahab, N. Ahmad, M. Alam, J. Ahmad. Vacuum 165 (2019) 290-296.

[71] A. A. Ibrahim, G. N. Dar, S. A. Zaidi, A. Umar, M. Abaker, H. Bouzid, S. Baskoutas. Talanta 93 (2012) 257-263.

[72] A. Umar, M. M. Rahman, Y. B. Hahn. Talanta. 77 (2009) 1376-1380.

[73] M. M. Rahman, S. B. Khan, A. Jamal, M. Faisal, A. M. Asiri. Sensors & Transducers Journal. 134 (2011) 32-44.

[74] H. B. Balkhoyor, M. M. Rahman, A. M. Asiri. RSC Adv. 6 (2016) 58236.

[75] M. M. Rahman, S B Khan, A. M. Asiri. Microchim Acta. 181 (2014) 553-563.

[76] S. B. Khan, M. Faisal, M. M. Rahman, A Jamal. Talanta. 85 (2011) 943-949.

[77] M. M. Rahman, A. M. Asiri. Sensors and Actuators B. 214 (2015) 82-91.

[78] M. M. Rahman, S. B. Khan, A. M. Asiri, H. M. Marwani, A. H. Qusti. Composites: Part B Engineering. 54 (2013) 215-223.

[79] H. M. Nassef, A. Radi, C. K. O'Sullivan. J. Electroanal. Chem. 592 (2006) 139-146.

[80] M. R. Akhgar, M. S. H. Zamani, A. Changizi, H. Hosseini-Mandiabad. Int. J. Electrochem. Sci. 8 (2013) 520-534.

[81] M. M. Alam, A. M. Asiri, M. M. Rahman Material. Chem. Phys. 243 (2020) 122658.

[82] Terti, M., Florea, A., Adumitrăchioaie, A., Cernat, A., Bogdan, D., Barbu-Tudoran, L., Jaffrezic Renault, N., Săndulescu, R., Cristea, C. Chempluschem 82 (2017) 561-569.

[83] Alizadeh, T., Azizi, S. Biosens. Bioelectron. 81 (2016) 198-206.

[84] Huo, K., Li, Y., Chen, R., Gao, B., Peng, C. Zhang, W., Hu, L., Zhang, X., Chu, P. K. ChemPlusChem 80 (2015) 576-582.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An electrochemical sensor, comprising:
a nanocomposite comprising zinc oxide nanoparticles, graphene oxide, and poly(3,4-ethylenedioxythiophene) polystyrene sulfonate (PEDOT:PSS) binder polymer, wherein the nanocomposite is deposited as a film on a glassy carbon electrode.

2. The electrochemical sensor of claim 1, wherein the film has a thickness of 0.1-1.0 μm.

3. The electrochemical sensor of claim 1, wherein the nanocomposite has a band-gap energy of 2-6 eV.

4. An electrochemical cell, comprising the electrochemical sensor of claim 1 and a counter electrode.

5. The electrochemical cell of claim 4, wherein the counter electrode is platinum.

6. A method for detecting phenylhydrazine in a solution, comprising
contacting the solution with the electrochemical cell of claim 4; and
detecting a change in current indicative of phenylhydrazine transformation.

7. The method of claim 6, wherein the solution is at a pH of 7.3-7.7.

8. The method of claim 6, wherein the change in current is detected within 10 seconds of the contacting step.

9. The method of claim 6, wherein the concentration of phenylhydrazine in the solution is less than 0.03 nM.

* * * * *